(12) United States Patent
Ciftci

(10) Patent No.: US 11,654,119 B2
(45) Date of Patent: May 23, 2023

(54) BIOAVAILABLE CURCUMIN NANOPARTICLES AND METHODS OF MAKING

(71) Applicant: NUtech Ventures, Lincoln, NE (US)

(72) Inventor: Ozan N. Ciftci, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 326 days.

(21) Appl. No.: 17/260,655

(22) PCT Filed: Jul. 18, 2019

(86) PCT No.: PCT/US2019/042355
§ 371 (c)(1),
(2) Date: Jan. 15, 2021

(87) PCT Pub. No.: WO2020/018759
PCT Pub. Date: Jan. 23, 2020

(65) Prior Publication Data
US 2021/0259992 A1   Aug. 26, 2021

Related U.S. Application Data

(60) Provisional application No. 62/699,904, filed on Jul. 18, 2018.

(51) Int. Cl.
*A61K 31/12*  (2006.01)
*C08J 9/40*   (2006.01)
(Continued)

(52) U.S. Cl.
CPC ............... *A61K 31/12* (2013.01); *A61K 9/06* (2013.01); *B01D 11/0203* (2013.01); *C08J 9/28* (2013.01); *C08J 9/40* (2013.01); *C08J 2205/026* (2013.01)

(58) Field of Classification Search
CPC ........ A61K 31/12; A61K 9/06; A61K 8/0279; A61K 8/732; A61K 8/9794; A61K 2800/412; A61K 36/9066; B01D 11/0203; C08J 9/28; C08J 9/40; C08J 2205/026; C08J 2201/05; C08J 2205/042; C08J 2207/10; C08J 2303/02; Y02P 20/54; A61Q 1/04
See application file for complete search history.

(56) References Cited

U.S. PATENT DOCUMENTS

2018/0207546 A1   7/2018   Ciftci

FOREIGN PATENT DOCUMENTS

FR   3053247   1/2018

OTHER PUBLICATIONS

Ahmed et al., "Nanoemulsion- and emulsion-based delivery systems for curcumin: Encapsulation and release properties," Food Chemistry, 132 (2012) 799-807 (Year: 2012).*
(Continued)

*Primary Examiner* — Kara B Boyle
(74) *Attorney, Agent, or Firm* — Stinson LLP

(57) ABSTRACT

Formation of low-crystallinity curcumin nanoparticles via controlled supercritical carbon dioxide (SC-$CO_2$) impregnation of curcumin into biodegradable nanoporous starch aerogels and methods of preparing these aerogels are disclosed. The nanoporous starch aerogels increase water solubility and bioaccessibility of the curcumin, thereby making them available for preparation of high nutraceutical value foods.

14 Claims, 10 Drawing Sheets

(51) Int. Cl.
    A61K 9/06      (2006.01)
    B01D 11/02     (2006.01)
    C08J 9/28      (2006.01)

(56) References Cited

OTHER PUBLICATIONS

Yu et al., "Enhanced in vitro anti-cancer activity of curcumin encapsulated in hydrophobically modified starch," Food Chemistry, 119 (2010) 669-674 (Year: 2010).*
Alemany et al., Effect of simulated gastrointestinal digestion on plant sterols and their oxides in enriched beverages, Food Research International, 2013, vol. 52, No. 1, pp. 1-7.
Dharunya et al., Curcumin cross-linked collagen aerogels with controlled anti-proteolytic and 1, 2, 12-14 pro-angiogenic efficacy, Biomedical Materials, 2016, vol. 11, No. 10, 18-pages.
Gurikov et al., Non-Conventional Methods for Gelation of Alginate, Gels, vol. 4, No. 1, 01 Feb. 1-14, 2018.
Mennah-Govela & Bornhorst et al., Mass transport processes in orange-fleshed sweet potatoes leading to structural changes during in vitro gastric digestion, Journal of Food Engineering; 2016, vol. 91, pp. 48-57.
Minekus et al., a Standardised Static in Vitro Digestion Method Suitable for Food—An International Consensus; Food & Function, 2014, vol. 5, No. 6, pp. 113-1124.
Prasad et al., Precipitation of curcumin by pressure reduction of CO2-expanded acetone; Powder Technol, 2017, vol. 310, pp. 143-153.
Rein et al., Bioavailability of bioactive food compounds: a challenging journey to bioeffficacy; 2013, British Journal of Clinical Pharmacology; vol. 75, No. 3, pp. 588-602.
Sigfridsson, et al., Particle size reduction for improvement of oral absorption of the poorly soluble drug UG558 in rats during early development, Drug Development and Industrial Pharmacy, 2009, vol. 35, No. 12, pp. 1479-1486.
Ubeyitogullari et al., Formation of nanoporous aerogels from wheat starch. Carbohydr. Polym. 2016. ,vol. 147, pp. 125-132.
Ubeyitogullari et al., Phytosterol nanoparticles with reduced crystallinity generated using 1, 2, 12-14 nanoporous starch aerogels, RSC Adv., vol. 6, 2016.
Williams et al., Size and dose deendent effects of silver nanoparticle exposure on intestinal permeability in an in vitro model of the human gut epithelium; Journal of Nanobiotechnology; 2016, vol. 14, No. 62, 13-pages.

* cited by examiner

FIG. 11A                    FIG. 11B

BIOAVAILABLE CURCUMIN NANOPARTICLES AND METHODS OF MAKING

CROSS REFERENCE TO RELATED APPLICATIONS

This application is a national phase application based on PCT/US2019/042355, filed Jul. 18, 2019, which claims priority to U.S. Provisional Application Ser. No. 62/699,904 filed Jul. 18, 2018, both of which are hereby incorporated by reference in their entireties.

BACKGROUND OF THE DISCLOSURE

The present disclosure relates generally to the formation of low-crystallinity curcumin nanoparticles to enhance the bioavailability of curcumin. Particularly, it has been found that these nanoparticles and method of the curcumin nanoparticle formation provides food grade curcumin with reduced crystallinity and increased bioaccessibility, thereby making it available for preparation of high nutraceutical value foods or health and wellness-improving supplements in the powder or capsule form.

Epidemiologic evidence increasingly demonstrates a central protective role of diets rich in plant phenolics from fruits and vegetables, legumes, and whole grains on different cancers, gastrointestinal diseases, and cardiovascular diseases. While Americans declare wanting to increase their consumption of fruit and vegetables as they try to maintain healthier lifestyles, the consumption of fruits and vegetables in the U.S. increased modestly by 8% (fruits) and 24% (vegetables) from 1977-1979 to 1997-1999. Produce availability throughout the year, geographically diverse production patterns, costs involved in transportation, and short shelf life may restrict their consumption by the populace on a regular basis to have impact on human health. As a complementary measure, the consumption of phenolics from plant extracts is encouraged. Convenience is increasingly important for consumers when selecting fruit and vegetables, and for that reason, most Americans consume produce in processed forms. The food industry has recognized the trend in functional foods popularity and is making efforts to increase their production. In recent years, consumers' interests have evolved beyond satiation and calories to include food for health and wellness. Environmental and health concerns have tempered the popularity of foods containing artificial ingredients, spurring the food industry to develop bioactive-rich foods and beverages.

Curcumin (diferuloylmethane) is a polyphenolic compound which is mainly extracted from turmeric rhizome (*Curcuma longa*). It has been used in Ayurvedic medicine as a traditional pharmaceutical agent for thousands of years. The health benefits of curcumin are well-documented; specifically, curcumin exhibits anticancer, antiviral, antioxidant, anti-inflammatory, antimicrobial, hypoglycemic, and anti-rheumatic properties. Moreover, therapeutic applications of curcumin in the treatment of cancer, diabetes, cardiovascular diseases, neurodegenerative diseases, and gastrointestinal irritation are well established. Curcumin is also safe at high doses (12 g/day) as studied in human clinical trials. However, the bioavailability of curcumin in humans is very low (~1%) due to its low water solubility, chemical instability and high melting point crystalline structure. Furthermore, low water solubility and crystalline structure limit the incorporation of curcumin into foods due to the negative effects on the sensory and quality of the product.

In recent years, there has been many research efforts to decrease the size of curcumin, and in turn, to increase its bioavailability as decreasing the size of bioactives is known to improve their solubilization and thereby their bioavailability. Different approaches have been implemented for this purpose including emulsion formulations, cyclodextrin complexes, synthesis of colloidal particles, nanosuspensions by antisolvent precipitation, and polysaccharide complexes. However, the use of organic toxic solvents (i.e., chloroform) and surfactants limit their applications in food products; furthermore, most of those techniques produce liquid products which are difficult to handle and store. In addition, curcumin has low stability in aqueous medium, which could be another disadvantage of those liquid formulations. Emulsions have several drawbacks associated with their food applications, including: (i) they produce liquid products which are difficult to handle and store; (ii) emulsions may not be stable when incorporated into real-food formulations due to change in the concentration of the surfactants used; and (iii) they may have a negative impact on the food quality and may be applicable to only a certain type of food. The proposed technique in the present disclosure overcomes those problems by producing dry formulations which can be easily incorporated into different food types.

Another approach to decrease the size of curcumin is based on supercritical carbon dioxide ($SC-CO_2$) technology which implements $CO_2$ as a green, non-toxic, inexpensive and abundant solvent. So far, solid lipid particles by Particles Generated from Gas Saturated Solution (PGSS), micronization by Atomized Rapid Injection Solvent Extraction (ARISE), loading nanofibrous silk fibroin by Solution-Enhanced Dispersion via $SC-CO_2$ (SEDS), and Precipitation by Pressure Reduction of Gas-Expanded Liquids (PPRGEL) have been employed to decrease the size of curcumin using $SC-CO_2$. However, the difficulty in controlling the particle size, the use of organic solvents like acetone, and limited number of food-grade chemicals used during the production are still significant problems with the current techniques. Moreover, none of those methods showed any data on the improvement in the bioavailability of curcumin Therefore, there is a critical need for a novel food-grade approach to decrease the size and crystallinity of curcumin and in turn to improve curcumin's bioavailability.

BRIEF DESCRIPTION OF THE DISCLOSURE

The present disclosure is generally related to curcumin nanoparticles with reduced crystallinity (CUR-NP) and increased bioavailability. Developing low-crystallinity curcumin nanoparticles impregnated in nanoporous starch aerogels (NSA) will make the addition of crystalline curcumin into foods and beverages to produce health and wellness improving foods in a clean and simple way, and maximize the utilization of curcumin.

Accordingly, in one aspect, the present disclosure is directed to a nanoporous starch aerogel impregnated with curcumin.

In another aspect, the present disclosure is directed to a method of forming a starch aerogel impregnated with curcumin, the method comprising: forming a nanoporous starch aerogel by: exchanging water in the starch hydrogel with ethanolic curcumin solution to form an alcogel; and $SC-CO_2$ drying the alcogel to form the nanoporous starch aerogel impregnated with low-crystallinity curcumin.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 4A-4D depict scanning electron microscope (SEM) images of the crude curcumin (FIG. 4A), curcumin precipitated from ethanol without NSA (FIG. 4B), and CUR-NP (FIG. 4C & FIG. 4D).

FIGS. 7A, 7D, and 7G depict images of the surface of NSAs; FIGS. 7B, 7E, and 7H depict low magnification images of the center of NSAs; and FIGS. 7C, 7F, and 7I depict high magnification images of the center of NSAs.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed to low-crystallinity curcumin (CUR) nanoparticles impregnated in nanoporous starch aerogels (NSA) (also referred to herein as curcumin nanoparticles or CUR-NP) and methods of making and impregnating these nanoparticles. As noted above, curcumin is a polyphenolic compound which is mainly extracted from turmeric rhizome (*Curcuma longa*). The health benefits of curcumin include uses such as anticancer, antiviral, antioxidant, anti-inflammatory, antimicrobial, hypoglycemic, and antirheumatic uses. Moreover, therapeutic applications of curcumin in the treatment of cancer, diabetes, cardiovascular diseases, neurodegenerative diseases, and gastrointestinal irritation are well established. Curcumin has also very low toxicity. Although the health benefits of CUR are well recognized, the incorporation of CUR into foods is a major challenge from a technological and food quality standpoint because crude CUR is a crystalline powder that is insoluble in water and poorly soluble in fats and oils. Its poor water solubility markedly limits its bioavailability. This is because as crystals, lipophilic bioactives are typically not water soluble, and thus poorly bioavailable; in contrast, amorphous forms are water soluble and more bioavailable. Therefore, there is a critical need for a new method that decreases the crystallinity of CUR.

Figure 1:
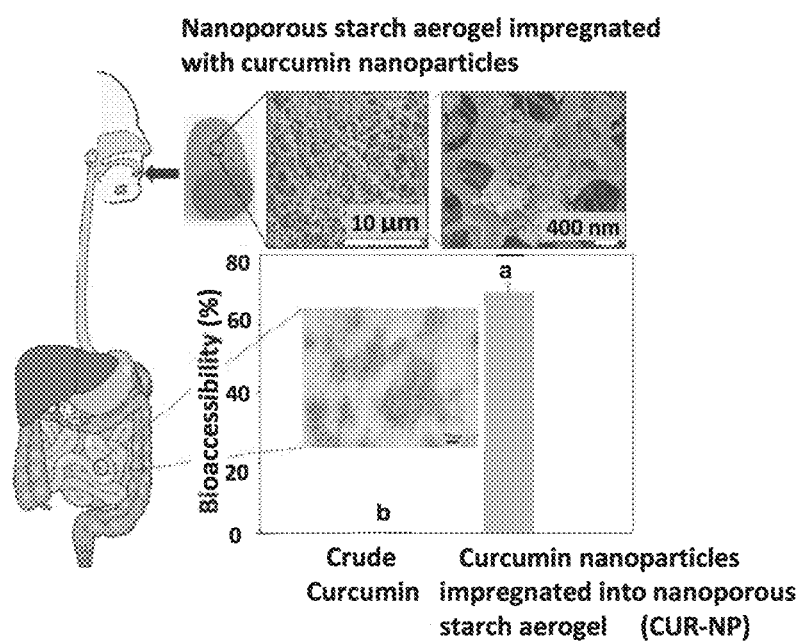
FIG. 1 depicts that the bioaccessibility of CUR-NP (CUR nanoparticles impregnated in nanoporous starch aerogels (NSA)) was markedly superior to that of crude CUR in simulated digestion.

FIG. 1. The bioaccessibility of CUR-NP (CUR nanoparticles impregnated in nanoporous starch aerogels) is markedly superior to that of crude CUR in simulated digestion.

It has been found that the controlled impregnation of CUR into nanoporous starch aerogel (NSA) using supercritical carbon dioxide (SC-$CO_2$) as accomplished by the present disclosure can be used to markedly increase CUR dissolution in water and potentially its bioavailability in the GI tract (FIG. 1). The disclosed method enhances the function and efficacy of CUR by producing the first-of-its-kind low-crystallinity CUR nanoparticles (CUR-NP) using NSA and SC-$CO_2$ technology.

The expected outcomes include (i) the development of a food-grade CUR formulation with enhanced efficacy in human health; (ii) the blueprint to apply to other water-insoluble food bioactives; (iii) the transfer of green technology to food manufacturers. This approach will (i) improve public health through valorization of a popular nutrient; (ii) enhance the cost-benefit ratio of water-insoluble bioactives; (iii) avert toxic chemicals & environmental pollution; and (iv) lower the costs of handling, storage & transportation of bioactives.

The nanoparticles for use in incorporating curcumin are made from aerogels, which have been attracting a growing interest due to their outstanding surface area, porous structure, and light weight. The present disclosure proposes two innovative approaches, using nanoporous starch aerogels as a material for colloid/nanoparticle formation for incorporating curcumin, and an impregnation method using SC-$CO_2$ to form curcumin nanoparticles with reduced crystallinity and in turn enhanced bioavailability.

Starch is a promising low cost, renewable, abundant, and bio-based source for aerogel formation. Suitable starches for use as the starch aerogel in the curcumin nanoparticles of the present disclosure include wheat starch and corn starch. Among starch sources, wheat starch is the third most produced starch type in the world, and it has the potential for the formation of starch hydrogels with three dimensional polymeric network structures and it has an important role in many foods. Wheat starch is comprised of 25% amylose and 75% amylopectin. Amylose is a linear polymer of $\alpha[1\rightarrow4]$ linked D-glucose. On the other hand, amylopectin is a branched polymer with $\alpha[1\rightarrow4]$ and $\alpha[1\rightarrow6]$ bonds and has higher molecular weight than amylose. Currently, wheat has limited uses, mainly for flour production, therefore the use of wheat starch to produce high value aerogel products may maximize the utilization of wheat and add value to wheat. Wheat starch aerogels with their outstanding properties will provide many opportunities for food applications, and bioactive protection and delivery. Accordingly, in one particularly suitable embodiment, the starch aerogel is wheat starch aerogel.

As used herein, the starch aerogels are nanoporous. As used herein, "nanoporous" refers to aerogels having a regular, porous structure, where the average Barrett-Joyner-Halenda (BJH) pore size is 20 nanometers or smaller. The nanopores of the nanoporous starch aerogel (NSA) act as a mold to prevent the formation of bigger crystals and lead to the formation of curcumin nanoparticles whilst decreasing their crystallinity, which later leads to the enhanced solubility of curcumin in water and gastrointestinal fluid, thus, enhancing the curcumin bioassessibility and bioavailability. As described more fully in the Examples below, the curcumin nanoparticles significantly enhanced bioaccessibility of curcumin by 173-fold more compared to the original crude curcumin.

It has been found that impregnation of curcumin into nanoparticles decreased the crystallinity of curcumin and did not create any chemical bonding between curcumin nanoparticles and the NSA matrix. This approach produced food grade low-crystallinity curcumin nanoparticles that had maximized the utilization of curcumin due to increased bioaccessibility.

In accordance with other embodiments of the present disclosure, methods of forming the nanoporous starch aerogels and use of the formed aerogels for impregnation of curcumin are disclosed.

Methods of Making Curcumin Nanoparticles

Figure 2:
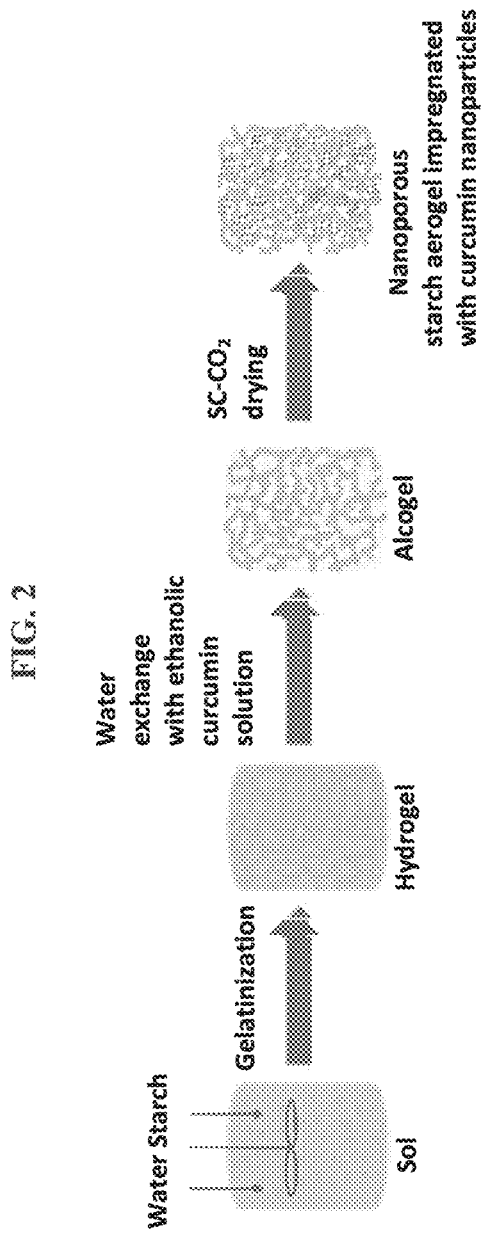
FIG. 2 depicts the process of formation of NSA impregnated with low-crystallinity CUR nanoparticles using the simultaneous aerogel formation-impregnation method.

Typically, the method of forming a starch aerogel impregnated with curcumin includes: forming a starch hydrogel; exchanging the water in the hydrogel with an ethanolic curcumin solution to form an alcogel; and supercritical carbon dioxide ($SC-CO_2$) drying of the alcogel to remove the ethanol from the alcogel (FIG. 2). To form the nanoporous starch aerogel, a starch hydrogel is formed; water in the starch hydrogel is exchanged with ethanol to form an alcogel; and the alcogel is $SC-CO_2$ dried to form the nanoporous starch aerogel.

The starch hydrogel is typically formed by gelatinizing starch. For example, in one embodiment, the starch is gelatinized at a temperature ranging from about 80° C. to about 140° C. to form a three-dimensional starch hydrogel. The starch hydrogel suitably includes from about 5% to about 15% by weight starch, and suitably, about 10% by weight starch.

Generally, to form an alcogel, the methods include solvent exchanging water in the starch hydrogel with ethanol by immersing the starch hydrogel in an ethanol solution. In one suitable embodiment, the ethanol solution includes from about 30% v/v to 100% v/v ethanol. The immersion of the starch hydrogel can occur in one solution of ethanol or multiple solutions of ethanol. Further, the ethanol solutions can vary in ethanol concentration. The starch hydrogels are immersed for a time period of from about 30 minutes to about 48 hours, and suitably from about 1 hour to about 24 hours. For example, in one particularly suitable embodiment, the starch hydrogel is immersed in a first ethanol solution comprising about 30% v/v ethanol for a first time period of about 1 hour, the starch hydrogel is immersed in a second ethanol solution comprising about 50% v/v ethanol for a second time period of about 1 hour, the starch hydrogel is immersed in a third ethanol solution comprising about 70% v/v ethanol for a third time period of about 1 hour, the starch hydrogel is immersed in a fourth ethanol solution comprising 100% v/v ethanol for a fourth time period of about 1 hour, and the starch hydrogel is immersed in a fifth ethanol solution comprising 100% v/v ethanol for a fifth time period of about 24 hours.

Supercritical fluid technology, and particularly, $SC-CO_2$ has proven itself as an efficient and environmentally friendly technology and has found use in the extraction of lipids from a variety of natural materials, and, in particle formation as a new promising application of supercritical fluids. Particularly, $SC-CO_2$ is used as a solvent for lipid and lipophilic bioactive extraction, medium for enzymatic reactions, atomizer for micro- and nanoparticle formation, dryer for aerogel formation, and solvent/carrier for impregnation. Unique tunable properties, and advantages of nontoxicity, nonflammability, low cost, availability in large quantities, tunable solvent properties, and moderate critical temperature and pressure of $SC-CO_2$ allow for the development of green methods and products that cannot be possible with conventional technologies. Generally, the $SC-CO_2$ drying of the alcogel to form the aerogel includes $SC-CO_2$ extraction as known in the $SC-CO_2$ drying art.

Figure 3:
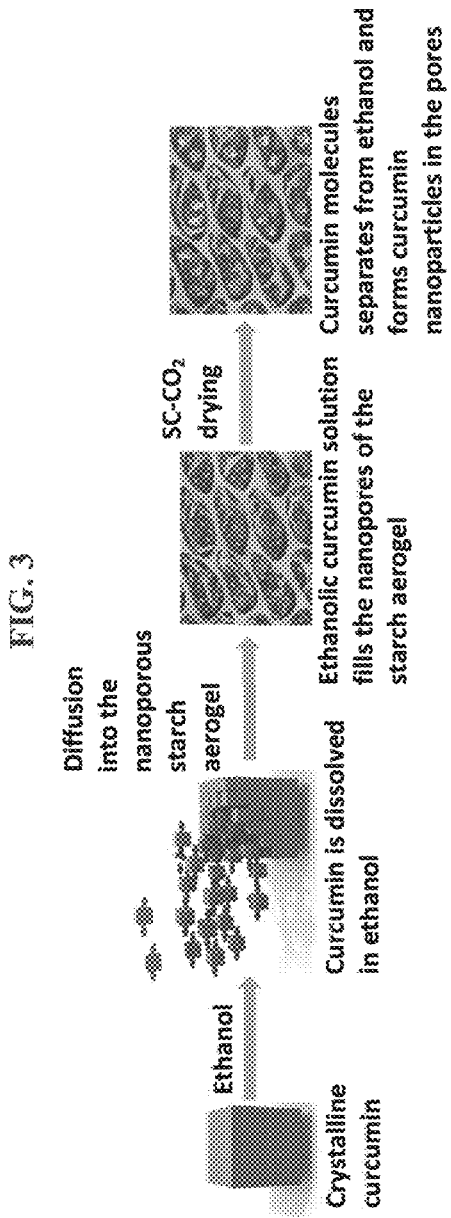
FIG. 3 depicts the mechanism of the size and crystallinity reduction of CUR via impregnation into NSA using SC-$CO_2$.

The methods of the present disclosure further utilized the nanopores and large surface area of NSA as a cast to decrease the size and crystallinity of CUR by controlling its recrystallization using $SC-CO_2$ (FIG. 3). CUR was first dissolved in ethanol. Ethanol is used to dissolve CUR because it is a food-grade solvent and ethanol is efficiently extracted with $SC-CO_2$. All non-food grade chemicals and solvents were removed from the process. Particularly, crystalline curcumin is dissolved in ethanol. Next, this ethanolic CUR solution was used in the solvent exchange step mentioned above to replace water in the hydrogel with ethanolic CUR. During this step, ethanolic CUR solution filled the nanopores of the hydrogel, displacing water by concentration gradient, and formed an alcogel. In the last step, the alcogel loaded with ethanolic CUR was dried with $SC-CO_2$ at 40° C. and 10 MPa. During $SC-CO_2$ drying, $SC-CO_2$ removes ethanol and forms NSA. By absence of ethanol, CUR molecules simultaneously precipitate in the nanopores of NSA, which act as a mold and a physical barrier thereby preventing the formation of large, well-ordered CUR crystals.

Figures 4A, 4B, 4C:
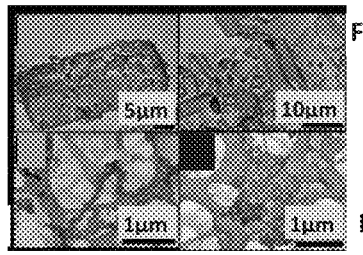

When CUR was recrystallized from the ethanolic solution using $SC-CO_2$ drying, but in absence of NSA, very large CUR crystals (~5-15 μm) (FIG. 4B) were obtained, revealing the critical role of NSA in CUR nanoparticle formation. NSA's large surface area allowed the formation of CUR nanoparticles <100 nm in size, which is advantageous in terms of dissolution rate in digestive fluids. Scanning electron microscopy (SEM) images of crude CUR revealed that CUR is highly crystalline with well-ordered crystals of >20 μm in size (FIG. 4A); in contrast, CUR-NP particles produced by this method averaged 80 nm (FIGS. 4C & 4D). CUR impregnation capacity was 224 mg CUR/g NSA, which is higher than any other CUR delivery systems reported in the literature.

Figure 5:
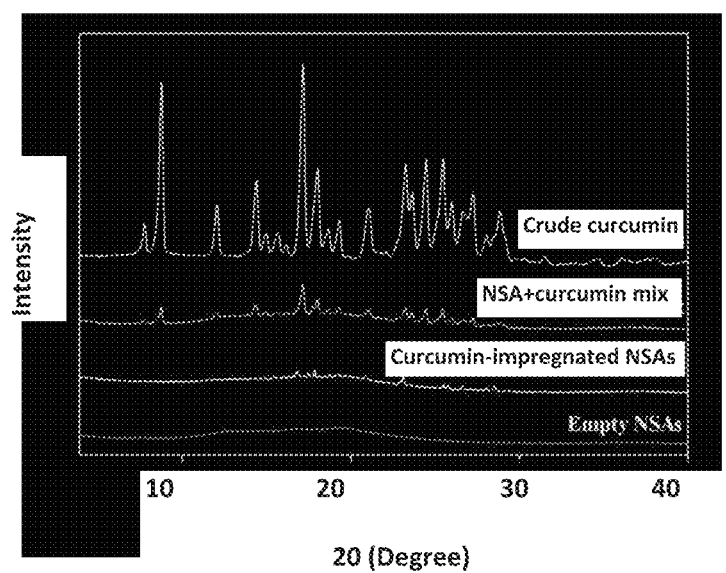
FIG. 5 depicts X-ray diffraction patterns of crude curcumin, physical mixture of crude curcumin with empty NSA (14.4 mg crude curcumin/g empty NSA), curcumin-impregnated NSA, and empty NSA.
Figures 6A, 6B, 6C:
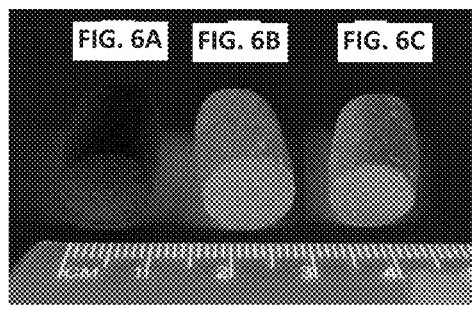
FIGS. 6A-6C depict pictures of empty NSA (FIG. 6A), curcumin-impregnated at 60° C. (CUR-NSA-60° C.) (FIG. 6B) and curcumin-impregnated NSA at room temperature (CUR-NSA-RT) (FIG. 6C).
Figures 7A, 7B, 7C, 7D, 7E, 7F, 7G, 7H, 7I:
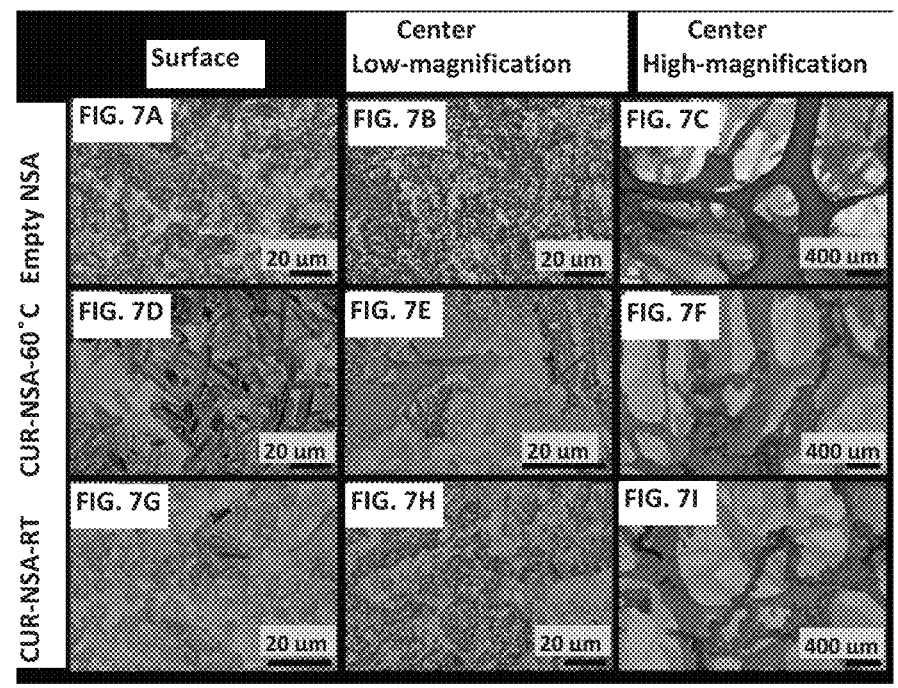
FIGS. 7A-7I depict SEM micrographs of empty NSA (FIGS. 7A-7C), curcumin-impregnated at 60° C. (CUR-NSA-60° C.) (FIGS. 7D-7F), and curcumin-impregnated NSA at room temperature (CUR-NSA-RT) (FIGS. 7G-7I).

X-ray diffraction (XRD) analysis confirmed that CUR-NP was less crystalline than crude CUR (FIG. 5). It was also confirmed by ATR-FTIR spectroscopy that there was no chemical bonding between NSA and CUR-NP (FIGS. 6A & 6B). This is important for the release of CUR-NP from NSA during digestion thereby affording high bioaccessibility.

Methods of Using the Curcumin Nanoparticles

Inflammation contributes to cancer initiation and progression. Compelling data support the notion that inflammation is a critical component of tumor progression. It is now becoming clear that the tumor's microenvironment is largely orchestrated by inflammatory cells; and inflammation contributes actively in the neoplastic and proliferative processes. Normal inflammation is self-limiting, because the production of anti-inflammatory cytokines closely follows that of pro-inflammatory cytokines. However, chronic inflammation seems to be due to the persistence of initiating factors or a failure of mechanisms designed to resolve the inflammatory response.

How CUR exerts its health properties is not clearly known. CUR inhibits a number of different molecules that play a role in inflammation such as TNFα, cyclooxygenase-2, inducible nitric oxide synthase, NFκB in several types of cancer, but the master target of CUR in the pro-inflammatory cascade is not known. Noteworthy, CUR inhibits mTORC1 in various human intestinal cells at physiological concentrations (2.5 µM) and has anti-proliferative properties starting at 1 µM. Most of the absorbed CUR is metabolized in intestine and liver, suggesting that enterocytes and hepatocytes are the main cell types impacted by CUR consumption.

Accordingly, the curcumin nanoparticles can be used to reduce inflammation and help to treat inflammatory diseases and disorders. Exemplary inflammatory diseases and disorders include cancer (e.g., liver and colon), inflammatory bowel disease, diabetes, cardiovascular diseases, neurodegenerative diseases, gastrointestinal irritation, and combinations thereof.

The following examples and procedures further illustrate specific embodiments of the invention; however, the following illustrative examples should not be interpreted in any way to limit the invention.

EXAMPLES

Example 1

In this Example, nanoparticles incorporating curcumin were prepared. The nanoparticles were analyzed for crystallinity and bioaccessibility of curcumin.

Materials and Methods

Materials

Wheat starch was kindly obtained from Manildra Milling Corporation (IA, USA). Crude curcumin was purchased from Acros Organics (NJ, USA). The composition of crude curcumin was determined by high-performance liquid chromatography (HPLC) and found to be 2.0±0.3% bisdemethoxycurcumin, 15.0±0.4% demethoxycurcumin, and 83.0±0.7% curcumin Liquid $CO_2$ (99.99% purity) was purchased from Matheson Tri-Gas, Inc. (PA, USA). Glacial acetic acid (≥99.7% purity) and acetonitrile (HPLC grade) were obtained from Fisher Chemical (NJ, USA) and ethanol (100%) was purchased from Decon Laboratories, Inc. (PA, USA).

α-Amylase (from *Bacillus subtilis*, 160,000 BAU/g, Cat. No. 100447) was purchased from MP Biomedicals (OH, USA). Pepsin (3,616 U/mg protein, Cat. No. P6887), pancreatin (neutral protease: 208 USP units/mg solid; α-Amylase: 223 units/mg solid; lipase: 38.5 USP units/mg solid, Cat. No. 7545), pancreatic lipase (419 U/mg protein, Cat. No. L3126) and bile extract (Cat. No. B8631) were all of porcine origin and purchased from Sigma-Aldrich (MO, USA). Lipase A "Amano" 12 lipase A12 (from fungus *Aspergillus niger*, 132,000 U/g) was kindly provided by Amano Enzyme Inc. (IL, USA). All other chemicals were of analytical grade.

2.2. Curcumin Impregnated Nanoporous Starch Aerogel (NSA) Formation

NSA monoliths were produced from wheat starch according to the method of Ubeyitogullari and Ciftci using the optimized NSA formation conditions (Ubeyitogullari and Ciftci (2016) Carbohydr Polym 147, 125-132, which is hereby incorporated by reference to the extent it is consistent herewith). Briefly, wheat starch solution (10 wt. %) was gelatinized in a closed high pressure reactor (4520 Bench Top Reactor, Parr Instrument Company, IL, USA) at 120° C. and 600 rpm for 20 minutes to obtain the hydrogels, which were subsequently retrograded at 4° C. for 48 hours. Then, hydrogels were converted to alcogels with a five-step solvent exchange (30, 50, 70, and 100% (v/v) ethanol for 1-hour residence time then 100% ethanol for 24 hours), and finally NSAs were obtained by removing ethanol from the alcogels using $SC-CO_2$ drying at 40° C. and 10 MPa for 4 hours with a $CO_2$ flow rate of 0.5 L/min (measured at ambient conditions). $SC-CO_2$ drying of the alcogels was carried out in a custom-made laboratory scale $SC-CO_2$ drying system, which employed double head high pressure syringe pump (Model 260D, Teledyne Isco Inc., NE, USA) for pressurization. Details of the $SC-CO_2$ drying system are provided in Ubeyitogullari & Ciftci, 2017, Journal of Food Engineering, 207, 99-107).

Impregnation of curcumin was conducted during the solvent exchange step. Excess curcumin was mixed with ethanol at room temperature (21° C.) and the undissolved curcumin was removed by filtration through a 0.45 µm pore-size filter. Then, the saturated curcumin solution was used in the last step of the solvent exchange instead of 100% ethanol, which resulted in diffusion of curcumin dissolved in ethanol into the nanopores of the aerogels. Afterwards, curcumin impregnated alcogels were dried using the same $SC-CO_2$ drying conditions. Moreover, curcumin impregnation was investigated at 60° C., where higher solubility of curcumin in ethanol was obtained. Curcumin impregnated NSAs were called CUR-NSA-60° C. or CUR-NSA-RT depending on the impregnation temperature of 60° C. or room temperature (RT), respectively. Curcumin impregnated NSAs were stored in the freezer at −18° C. until characterized.

2.3. Morphology

The morphology of the curcumin impregnated NSAs was analyzed by field emission scanning electron microscope (S4700 FE-SEM, Hitachi, Tokyo, Japan) under low vacuum mode at 5 kV and 15 mA. The specimens were mounted on aluminum stubs with double-side conductive carbon tape and then sputter-coated with a chromium layer under vacuum (Desk V HP TSC, Denton Vacuum LLC, NJ, USA) prior to analysis.

The morphology of the curcumin in the bioaccessible fraction after simulated digestion was analyzed by transmission electron microscopy (TEM) (H-7500 TEM, Hitachi, Tokyo, Japan) at an accelerating voltage of 80 kV. One drop of bioaccessible fraction was placed on 230 mm copper grids and air dried. Then, the samples were negatively stained with 1% phosphotungstic acid. After drying at room temperature (21° C.) for 8 hours, the samples were examined by TEM. Furthermore, particle size of curcumin was measured from the SEM/TEM images using ImageJ v. 1.50i software (public domain, National Institutes of Health, USA) and the results were stated as mean±standard deviation.

2.4. Crystallinity

Crystallinity of the curcumin impregnated NSAs, physical mixture of crude curcumin with empty NSA (14.4 mg crude curcumin/g empty NSA), empty NSA and crude curcumin was studied with x-ray diffraction (XRD) analysis using a PANalytical Empyrean Diffractometer (Empyrean, PANalytical B.V., Almelo, Netherlands) equipped with PIXcel$^{3D}$ detector. The instrument was operated with 1D detection at 45 kV and 40 mA. The powdered samples (mesh #20) were scanned from 2° to 40° (2θ) with a sampling interval of 0.05° and an angular scanning velocity of 0.927°/min

2.5. Fourier-Transform Infrared Spectroscopy

The chemical interaction between curcumin and NSA was studied by ATR-FTIR (Nicolet 380, Thermo Scientific, MA, USA). FTIR spectroscopy was performed between 4000 cm$^{-1}$ and 400 cm$^{-1}$ at spectral resolution of 4 cm$^{-1}$ with 128 scans. FTIR spectra were analyzed with Nicolet Omnic 8.3 software.

2.6. Determination of the Curcumin Impregnation Capacity

Curcumin was extracted from 0.1 g impregnated NSA by 15 mL of acetonitrile in an amber glass vial at room temperature (21° C.) for 2 hours with occasional vortexing. Then, NSAs were separated from the mixture by 0.45 μm pore-size filter. Filter cake and the vial were washed with 5 mL of acetonitrile five times and filtered using 0.45 μm pore-size filter Finally, the concentration of curcumin in the filtrate was determined using an HPLC method as described in Section 2.7 below. The impregnation capacity was reported as mg curcumin/g NSA.

2.7. Curcumin Analysis

Curcumin was quantified by an HPLC (Agilent 1100 Series, Agilent Technologies, Germany) equipped with a variable wavelength detector (VWD). Briefly, the samples were injected onto a reversed phase Gemini C18 110A column (150×4.6 mm, 5 μm; Phenomenex, CA, USA) and elution of curcumin was monitored by UV absorbance at 420 nm. The mobile phase consisted of acetonitrile and 5% acetic acid at a ratio of 45:55 (v/v). The detection was carried out at 30° C. with a flow rate of 0.8 mL/min and the injection volume was 20 μL. Quantification of curcumin was based on an external calibration curve which was prepared using standard curcumin acetonitrile solutions ranging from 0.1 to 50 μg/mL.

2.8. Simulated Digestion

Gastrointestinal digestion of the samples was simulated adopting the method described by Minekus et al., 2014, Food & Function, 5(6), 1113-1124. Gastrointestinal digestion consisted of a sequential oral, gastric and intestinal digestion. Simulated salivary fluid (SSF), simulated gastric fluid (SGF) and simulated intestinal fluid (SIF) were prepared using a method reported previously (Minekus et al., 2014). The digestion samples were curcumin-impregnated NSAs during the solvent exchange at room temperature (Curcumin-NSA-RT) and 60° C. (Curcumin-NSA-60C), and the physical mixture of crude curcumin with empty NSA as a control sample. The experiments were performed in 50 mL Erlenmeyer flasks. All digestion experiments were carried out in triplicate.

2.8.1. Oral Phase

First, the sample (0.25 g) and SSF electrolyte stock solution (3.5 mL) were added into the flask. Then, 0.5 mL of α-amylase solution (750 U/mL) was included to have a final mixture with 75 U/mL. Subsequently, 25 μL of 0.3 M CaCl$_2$ and 0.975 mL of deionized water were added. Finally, pH of the mixture was adjusted to pH 7.0 and the mixture was agitated in a shaking water bath (Precision SWB 27, Thermo Fisher Scientific, NH, USA) for 30 sec at 37° C. with a mixing rate of 150 rpm (Mennah-Govela & Bornhorst, 2016; Minekus et al., 2014).

2.8.2. Gastric Phase

After the oral digestion, oral bolus (5 mL) was mixed with SGF electrolyte stock solution (3.25 mL, pH 3.0) and the pH was adjusted to 3.0 using 1 M HCl (75 μL). Afterwards, 0.5 mL of porcine pepsin solution (40 000 U/mL) and 0.25 mL of fungal lipase (1000 U/mL) were added to the mixture. There is no commercial gastric lipase, and therefore, fungal lipase was included as an analogue to human gastric lipase. Then, 2.5 μL of 0.3 M CaCl$_2$ and 0.923 mL of deionized water were included into the flask. The final ratio of oral bolus to SGF was 50:50 (v/v). The final mixture was incubated at 37° C. for a digestion time of 2 hours in the shaking water bath (100 rpm). The pH of the mixture was monitored and kept at pH 3.0 using 1 M HCl.

2.8.3. Intestinal Phase

After the gastric digestion, 6.125 mL of SIF electrolyte stock solution (pH 7.0) was mixed with the gastric chyme (10 mL). Then, pancreatin solution was prepared in SIF electrolyte stock solution according to α-amylase activity, and therefore, 1.25 mL of pancreatin solution (3200 U/mL) was added into the mixture to achieve a final α-amylase activity of 200 U/mL. Moreover, the lipase activity of 2000 U/mL was achieved in the final mixture by adding extra porcine pancreatic lipase (3310 U) into the pancreatin solution. Then, 0.625 mL of fresh bile solution (320 mM, prepared in SIF), 20 μL of 0.3 M CaCl$_2$ and 1.95 mL of deionized water were added to the mixture and the pH was adjusted to pH 7.0 using 1 M HCl (30 μL). The final ratio of gastric chyme to SIF was 50:50 (v/v). Lastly, the final mixture was incubated at 37° C. for 2 hours in the shaking water bath (100 rpm). The pH of the mixture was checked and re-adjusted to pH 7.0 with 1 M HCl throughout the intestinal digestion.

2.8.4. Bioaccessible Fraction

The bioaccessible fraction after digestion was separated using the method of Alemany et al., 2013, Food Research International, 52(1), 1-7 Immediately after simulated digestion experiments, the flasks were placed into an ice bath to stop digestion. Then, bioaccessible fraction of the digested samples was attained by centrifugation at 4° C. at 4000 rpm for 90 minutes (Clinical 200, VWR International, Radnor, Pa., USA). The bioaccessibility (%) of curcumin was calculated as follows:

$$\text{Bioaccessibility (\%)} = \frac{\text{Curcumin in the bioaccessible fraction}}{\text{Total curcumin included}} * 100 \quad (1)$$

The concentration of curcumin in the bioaccessible fraction was determined using the HPLC method described above (Section 2.7). The samples were filtered through 0.45 μm pore-size filter prior to analysis.

2.9. Statistical Analysis

Statistical analysis of the obtained data was performed using MINITAB® 16.1.1 software (Minitab Inc., State Collage, Pa., USA). Tukey's multiple comparison test was applied and the differences among treatments were considered to be statistically significant when p<0.05.

3. Results and Discussion

NSA formation included several major steps: gelatinization of wheat starch to form hydrogels, replacing the water in the hydrogels with ethanol to produce alcogels, and finally SC-CO$_2$ drying of the alcogels to generate aerogels. Gelatinization of starch results in swelling of the granules, amylose leaching and disruption of the ordered structure. On cooling, swollen granule sacs produce porous gel.

Solvent exchange was carried out prior to SC-$CO_2$ drying because ethanol has higher solubility than water in SC-$CO_2$. Drying of the alcogels is very crucial in order to preserve the porous structure of the gel. Previous studies have shown that air drying results in shrinkage of the structure and loss of all the pores due to high surface tension and capillary forces during drying. However, SC-$CO_2$ drying prevents the formation of liquid-vapor meniscus by eliminating the capillary forces in the pore walls (surface tension of the liquid in the pores). Therefore, SC-$CO_2$ drying preserved the nanoporous structure of the alcogels and generated NSAs with outstanding properties: surface area of 60.4±3.0 $m^2$/g, pore size of 19.9±2.5 nm, pore volume of 0.26±0.01 $cm^3$/g, density of 0.11±0.00 g/$cm^3$, and porosity of 92.8±0.2%.

Curcumin-ethanol solution diffused into the pores of the hydrogel during the last step of the solvent exchange and formed the alcogel. Then, ethanol in the curcumin-impregnated alcogel matrix was removed by SC-$CO_2$ drying. SC-$CO_2$ drying conditions were selected as 40° C., 10 MPa for 4 hours with a $CO_2$ flow rate of 0.5 L/min (measured at ambient conditions) based on previous studies where the drying temperature, pressure and flow rate of $CO_2$ were optimized for the highest NSA surface area (Ubeyitogullari & Ciftci, 2016a). During SC-$CO_2$ drying, curcumin was recrystallized from curcumin-ethanol-SC-$CO_2$ mixture in the pores of NSA, which acted as a template and prevented the formation of long and well-ordered curcumin crystals. In this approach, SC-$CO_2$ acts as an anti-solvent by reducing the solvent (ethanol) amount in the pores of the alcogel. As more ethanol is dissolved in SC-$CO_2$, curcumin starts to precipitate in the pores. Limited solubility of curcumin in SC-$CO_2$ at 10 MPa and 40° C. (~$4*10^{-7}$ g/L) prevented the extraction of curcumin from NSA during SC-$CO_2$ drying. Furthermore, this nanomanufacturing method eliminated the additional SC-$CO_2$ impregnation step after SC-$CO_2$ drying which was the case in a previous phytosterol nanoparticle formation study (Ubeyitogullari & Ciftci, 2016b).

This Example introduces a single-step green approach to generate low-crystallinity curcumin nanoparticles by utilizing SC-$CO_2$ technology. Few studies have reported formation of curcumin particles using SC-$CO_2$ technology by PGSS, PPRGEL, ARISE, and SEDS processes. PGSS technique uses $CO_2$ as a solute. In PGSS process, SC-$CO_2$ is dissolved in tristearin/soy phosphatidylcholine/DMSO/curcumin mixture and curcumin loaded solid lipid particles are produced by micronization of that mixture. PPRGEL, a similar method to PGSS, is employed to produce curcumin particles by atomization of curcumin/acetone solution into water. In addition, ARISE is based on atomization of a curcumin mixture into a vessel pressurized with $CO_2$. Feed solution is composed of curcumin/polyvinylpyrrolidone (PVP), hydroxypropyl-β-cyclodextrin (HPβCD), or both in organic solvents like methanol, ethanol or acetone. Furthermore, SEDS process is based on precipitation of curcumin from acetone solution in SC-$CO_2$. Curcumin-silk fibroin nanofibrous matrix is also produced using SEDS process. However, the current techniques do not provide a full control over the particle formation and result in particle agglomeration. The use of toxic solvents such as acetone and long complicated atomization procedures make those techniques not applicable in food industry. In this Example, aerogels have been utilized for the first time as a mold to produce curcumin nanoparticles. Moreover, this is the first study reducing the crystallinity of curcumin nanoparticles to improve curcumin's bioaccessibility.

3.1. Morphology

FIGS. 6A-6C depict pictures of empty NSA (FIG. 6A), curcumin impregnated NSA at 60° C. (CUR-NSA-60° C.; (FIG. 6B)) and curcumin impregnated NSA at room temperature (CUR-NSA-RT; (FIG. 6C)). Curcumin impregnated NSA had an even distribution of orange color in the matrix of aerogel monolith, which indicates a uniform diffusion of curcumin into the center of the monolith during solvent exchange. SEM images of empty NSA (FIG. 7A-7C), curcumin impregnated NSA at 60° C. (CUR-NSA-60° C.; (FIG. 7D-7F)) and curcumin impregnated NSA at room temperature (CUR-NSA-RT; (FIG. 7G-7I)) are presented in FIG. 7A-7I. Empty NSAs had three-dimensional open porous structure (FIGS. 7B & 7C) similar to previous studies (Ubeyitogullari & Ciftci, 2016, Carbohydrate Polymers, 147, 125-132; Ubeyitogullari & Ciftci, 2016, RSC Advances, 6(110), 108319-108327). This network structure was not affected by curcumin impregnation. Curcumin nanoparticles impregnated in the NSA had a spherical morphology and their average particle size was 71±8 and 66±9 nm in the CUR-NSA-60° C. and CUR-NSA-RT, respectively, as measured by Image J software from SEM images (FIGS. 7E, 7F, 7H & 7I). During SC-$CO_2$ drying, curcumin nanoparticles showed a tendency to form agglomerates due to hydrophobic effect. Recently, Prasad et al. (Powder Technol 310, 143-153, 2017) reported curcumin particle formation by PPRGEL process. The mean particle size of curcumin varied between 0.4 μm and 30.8 μm and the particles had a plate-like structure. Besides, PGSS technique formed curcumin loaded solid lipid particle agglomerates with sizes over 100 μm. Similarly, elongated thin curcumin crystals (~30 μm from ethanol and ~160 μm from acetone feed solutions) were fabricated with ARISE process. On the other hand, SEDS process generated irregular-shaped agglomerated curcumin particles with the smallest average particle size of 325 nm. However, those SC-$CO_2$ based techniques did not provide a good control over the particle size and morphology. In this Example, the formation of elongated curcumin crystals was prevented by the nanopores of the NSA.

3.2. Crystallinity

XRD patterns of the crude curcumin, physical mixture of crude curcumin with empty NSA (14.4 mg crude curcumin/g empty NSA), Curcumin-NSA-RT, and empty NSAs are presented in FIG. 5. The mass ratio of crude curcumin/empty NSA was determined according to the impregnation capacity of Curcumin-NSA-RT (Section 3.4 below). Crude curcumin had several strong characteristic peaks at 2θ=8.8°, 12.1°, 14.3°, 17.2°, 18.0°, 21.1°, 23.1°, 24.4°, 25.5°, 27.2°, and 28.8°, respectively. Similar diffraction peaks were observed in the literature for crude curcumin powder. These sharp peaks indicate the crystalline structure of crude curcumin. Empty NSAs had one broad peak, which means that empty NSAs were mainly in amorphous form due to disrupting the semi-crystalline structure of starch during gelatinization. The XRD pattern of the physical mixture of crude curcumin with empty NSA had the same characteristic diffraction peaks with the crude curcumin. However, the intensity of these peaks was much lower when curcumin was impregnated into NSA at the same mass ratio (FIG. 5). This indicated that curcumin was in a less crystalline form after impregnation into NSA due to recrystallization conditions. Curcumin in the CUR-NSA-60° C. had relatively higher crystallinity than that in CUR-NSA-RT due to higher amount of curcumin crystals on the surface. Reduced crystallinity enhances the dissolution rate of the water-insoluble bioactives due to the increase in the lattice free energy.

3.3. Fourier-Transform Infrared Spectroscopy

Figures 8A, 8B, 8C:
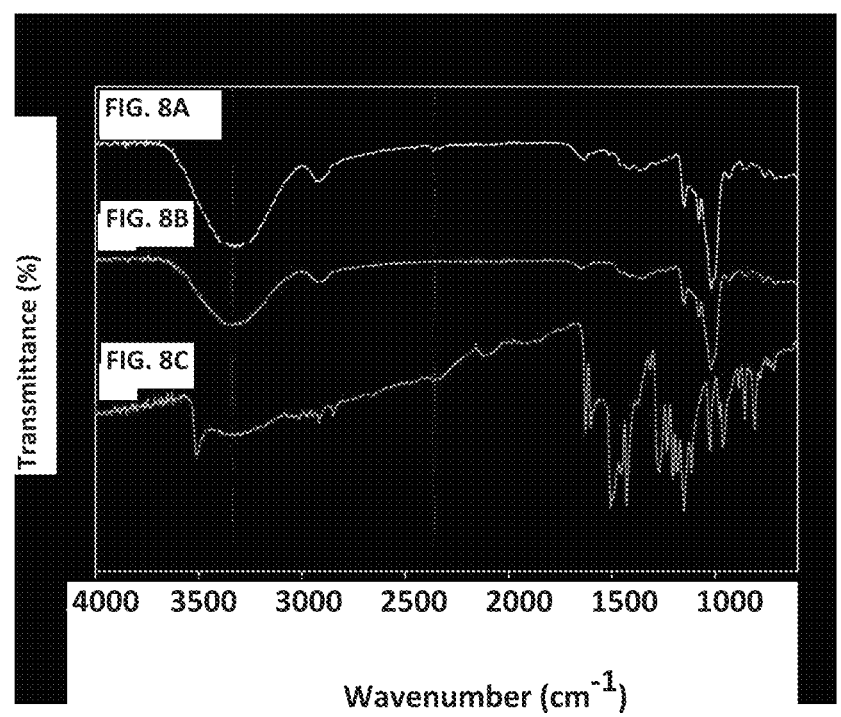
FIGS. 8A-8C depicts Attenuated Total Reflectance-Fourier Transform Infrared (ATR-FTIR) spectra of the (FIG. 8A) curcumin-impregnated NSA, (FIG. 8B) empty NSA, (FIG. 8C) crude curcumin.

The chemical interaction between curcumin and NSA was studied with ATR-FTIR (FIGS. 8A-8C). The FTIR results revealed that there was no shifting on the location of the characteristic peaks of crude curcumin, meaning there was no interaction between the curcumin particles and the NSA (FIGS. 8A & 8C). Absence of interaction between curcumin particles and NSA is desired because binding may affect the release of the curcumin particles during digestion negatively, which may lead to hindered bioaccessibility. Empty NSA (FIG. 8B) showed characteristic band between 3660 and 2990 $cm^{-1}$ for the O—H stretching; and exhibited peaks at 2900 $cm^{-1}$ for C—H stretching vibrations, 1150 $cm^{-1}$ for C—O—C glucosidic bridge, and 1180 and 1020 $cm^{-1}$ corresponding to C—C and C—O stretching vibrations. The FTIR spectrum of crude curcumin (FIG. 8C) exhibited a broad peak between 3450 and 3090 $cm^{-1}$ and a sharp peak at 3510 $cm^{-1}$ for O—H stretching; and peaks at 1625 $cm^{-1}$ for mixed C=O and C=C vibrations, 1602 $cm^{-1}$ for aromatic ring stretching vibrations, 1504 $cm^{-1}$ for C—O and C—C vibrations, 1427 $cm^{-1}$ for olefinic C—H bending vibrations, 1272 $cm^{-1}$ for aromatic C—O stretching vibrations, and 1025 $cm^{-1}$ for C—O—C stretching vibrations.

Impregnated curcumin nanoparticles tend to recrystallize close to each other. Having no interaction between the impregnated curcumin and NSA improves the release of curcumin in water or gastrointestinal tract after oral administration. Some other curcumin studies indicated a chemical bonding between curcumin and the formulation used which limits the release of curcumin

3.4. Impregnation Capacity

Impregnation capacity of the Curcumin-NSA-RT, where impregnation was performed at room temperature (21° C.), was 14.4 mg curcumin/g NSA (FIG. 5). When temperature of the impregnation increased to 60° C. (Curcumin-NSA-60C), the impregnation capacity significantly increased to 224.2 mg curcumin/g NSA (FIG. 5) ($p<0.05$). Impregnation capacity was basically based on the solubility of curcumin in ethanol. As the temperature of ethanol was raised from 21 to 60° C., the solubility of curcumin in ethanol increased from 4.4±0.2 to 17.2±0.3 mg curcumin/mL ethanol. The increase in the solubility was not exactly at the same order with the increase in the impregnation capacity; a 3.9-fold increase in the solubility of curcumin in ethanol resulted in 15.6-fold increase in the impregnation capacity. The reason for a drastic increase in the impregnation capacity at 60° C. was the crystallization of curcumin in the saturated ethanolic curcumin solution on the surface of the NSA due to temperature drop to 40° C. during SC-$CO_2$ drying. Crystallization from ethanol before the supercritical conditions reached led to the formation of long curcumin crystals (data not shown) which impacted the bioaccessibility of curcumin after simulated digestion (FIG. 10).

3.5. Simulated Digestion

Figure 9:
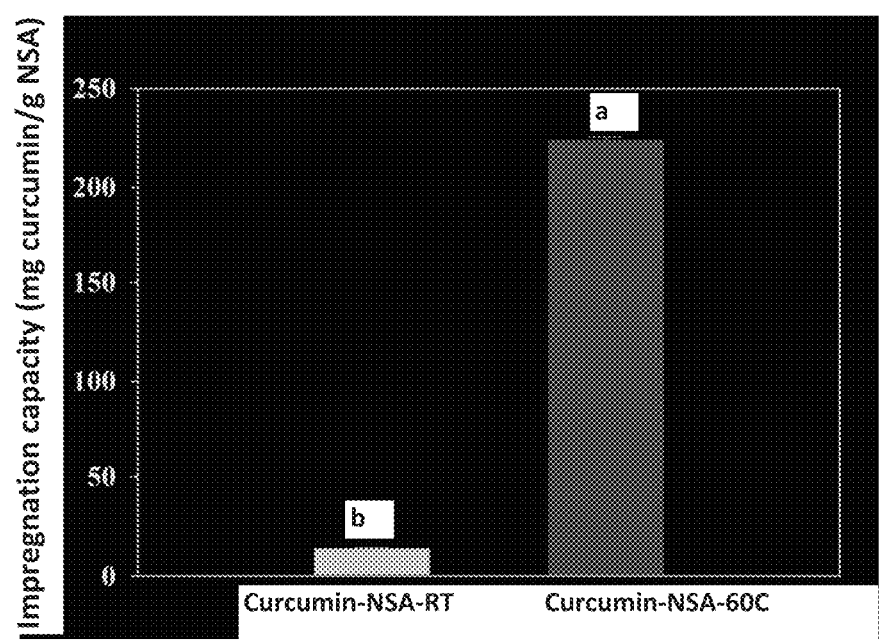
FIG. 9 depicts curcumin impregnation capacities of the NSAs generated at different impregnation temperatures. Curcumin-NSA-RT: impregnated at room temperature (21° C.), and Curcumin-NSA-60C: impregnated at 60° C.
Figure 10:
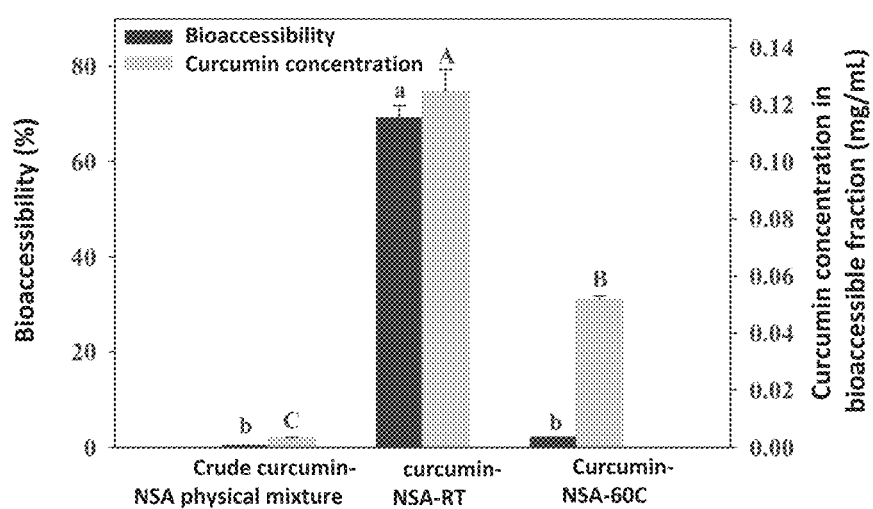
FIG. 10 depicts bioaccessibility and concentration of curcumin in the samples after simulated digestion as analyzed in the Example. Different lower-case letters show statistical significance in the bioaccessibility of curcumin ($P<0.05$) and different capital letters show statistical significance in curcumin concentration in the bioaccessible fraction of the samples ($P<0.05$).

Curcumin impregnated samples (Curcumin-NSA-RT and Curcumin-NSA-60C) underwent sequential oral, gastric, and intestinal digestion to determine the bioaccessibility and the concentration of curcumin in the bioaccessible fraction (FIG. 10). The physical mixture of crude curcumin with empty NSA was used as control. The bioaccessibility of crude curcumin was only 0.4% which was expected due to its low water solubility and crystalline structure. The bioaccessibility of curcumin was significantly improved with impregnation at room temperature (Curcumin-NSA-RT) ($p<0.05$). The bioaccessibility of curcumin nanoparticles (Curcumin-NSA-RT) was 173-fold higher than that of crude curcumin with a bioaccessibility of 69.1% (FIG. 10). Although the bioaccessibility of crude curcumin-NSA physical mixture (0.4%) and Curcumin-NSA-60C (2.2%) were not significantly different, Curcumin-NSA-60C (0.052 mg/mL) provided a significantly higher concentration of curcumin in the bioaccessible fraction than crude curcumin (0.003 mg/mL). The highest curcumin concentration (0.125 mg/mL) in the bioaccessible fraction was achieved with Curcumin-NSA-RT, which was 42 times higher than the concentration of crude curcumin in the bioaccessible fraction. Although the impregnation capacity of Curcumin-NSA-60C was significantly higher than that of Curcumin-NSA-RT (FIG. 9), both the bioaccessibility and curcumin concentration in the bioaccessible fraction of Curcumin-NSA-60C were significantly lower ($p<0.05$). As discussed before, curcumin had higher solubility in ethanol at 60° C. However, having high concentration of curcumin and the decrease in temperature to 40° C. during SC-$CO_2$ drying resulted in recrystallization of curcumin from ethanol solution and growth of crystals. As studied by SEM (data not shown), curcumin particles tend to form well-ordered plate-like crystals when recrystallized from organic solvents. Therefore, these plate-like curcumin crystals contributed to the increase in the impregnation capacity. However, they were not bioaccessible after simulated digestion due to larger sizes and led to a lower bioaccessibility and concentration in the bioaccessible fraction of Curcumin-NSA-60C.

Figures 11A, 11B:
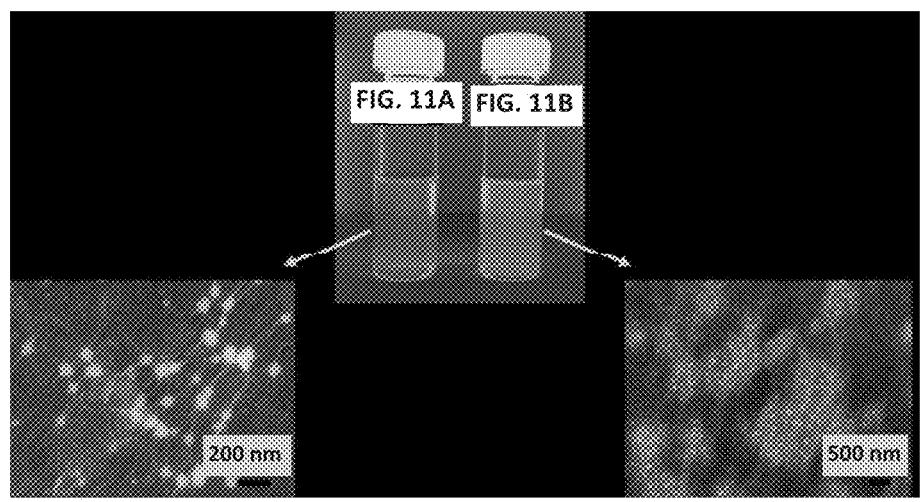
FIGS. 11A & 11B are pictures and transmission electron microscope (TEM) images of the bioaccessible fractions after simulated digestion of the (FIG. 11A) physical mixture of crude curcumin with empty NSA, and (FIG. 11B) CUR-NP.

FIGS. 11A & 11B depict photographs and TEM images of the bioaccessible fractions obtained after simulated digestion of the physical mixture of crude curcumin with empty NSA and Curcumin-NSA-RT. The color of the bioaccessible fraction of Curcumin-NSA-RT (FIG. 11B) was darker than that of crude curcumin (FIG. 11A), indicating a higher curcumin concentration. TEM images of the bioaccessible fractions revealed the particle size of the curcumin particles in the bioaccessible fractions. The particle size of curcumin particles in the bioaccessible fraction of Curcumin-NSA-RT (10±1 nm) was significantly smaller than that of crude curcumin (67±9 nm) ($p<0.05$). The smaller curcumin particles are expected to have higher absorption after digestion because of the higher permeability through biological barriers (Rein et al., 2013; Sigfridsson, Lundqvist, & Strimfors, 2009). To illustrate, silver nanoparticles (10, 20, 75 and 110 nm) were investigated at the same concentration for their epithelial permeability using T84 human colonic epithelial cells, and the particle size of 10 nm resulted in the highest permeability (Williams, Gokulan, Cerniglia, & Khare, 2016). Therefore, smaller curcumin particles in the bioaccessible fraction will lead to a higher bioavailability of curcumin due to higher absorption rates.

None of the studies using SC-$CO_2$ technology to form curcumin particles (PGSS, ARISE, SEDS and PPRGEL) determined the bioaccessibility of their products which is required in order to determine the stability and solubility of the curcumin particles in digestion fluids with changing environment like pH, and ionic strength. The results presented here provide a new nanomanufacturing method using SC-$CO_2$ technology and NSAs to fabricate low-crystallinity curcumin nanoparticles to improve the bioavailability of curcumin Curcumin nanoparticles were spherical in shape and their average size was 66 nm. The crystallinity of curcumin was decreased by impregnation into NSAs which enhanced the dissolution rate of curcumin in the digestive fluids and consequently improved its bioavailability. There was no chemical bonding between impregnated curcumin nanoparticles and the NSA, therefore release mechanisms of curcumin nanoparticles is improved. The highest impregnation capacity was obtained at an impregnation temperature of 60° C. as 224.2 mg curcumin/g NSA. However, the bioaccessibility of curcumin was maximized with an impregnation at room temperature. The highest bioaccessibility and concentration of curcumin in the bioaccessible fraction were 69.1% and 0.125 mg/mL, respectively. Curcumin nanoparticles had 173-fold higher bioaccessibility than crude curcumin and the concentration of curcumin in the bioaccessible fraction was significantly improved by impregnation into NSAs (42-fold).

Example 2

In this Example, nanoparticles incorporating curcumin were prepared. The nanoparticles were analyzed for crystallinity and bioaccessibility of curcumin.

Figure 12:
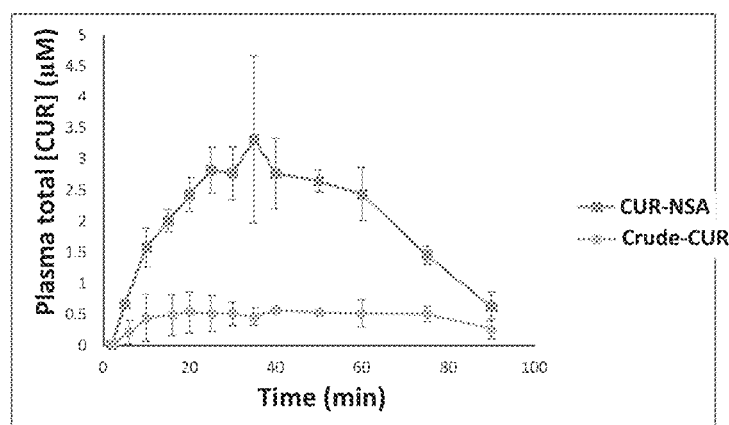
FIG. 12 depicts the bioavailability of curcumin (CUR) impregnated in the nanoporous starch aerogels in rats as analyzed in Example 2.

The plasma CUR concentration was monitored over time after administration. CUR-NSA upon administration resulted in higher CUR concentration in the serum over the entire time frame (0-90 minutes) investigated compared to the crude CUR. The plasma CUR concentration was considerably high in an extended period of time (15-75 minutes) when CUR-NSA was administered, suggesting a sustained release of CUR from the matrix. Moreover, the maximum concentrations of CUR in the plasma ($C_{max}$) after CUR-NSA and crude CUR administration were 3.3 and 0.5 µM, respectively, meaning 6.6-fold increase in the $C_{max}$ with CUR-NSA (see FIG. 12). These results suggest that CUR-NSA formation significantly enhances the absorption and in turn the bioavailability of CUR.

What is claimed is:

1. A nanoporous starch aerogel impregnated with curcumin.

2. The aerogel as set forth in claim 1 wherein the nanoporous starch aerogel is a wheat starch aerogel.

3. A method of forming a nanoporous starch aerogel impregnated with low-crystallinity curcumin, the method comprising:

forming a nanoporous starch aerogel by:
performing a solvent exchange by exchanging water in a starch hydrogel with ethanolic curcumin solution to form an alcogel; and
$SC-CO_2$ drying the alcogel to form the nanoporous starch aerogel impregnated with low-crystallinity curcumin.

4. The method as set forth in claim 3 wherein forming the starch hydrogel comprises gelatinizing starch at a temperature ranging from about 80° C. to about 140° C., wherein the starch hydrogel is a three-dimensional starch hydrogel.

5. The method as set forth in claim 4 wherein the starch hydrogel comprises about 10% starch.

6. The method as set forth in claim 4 wherein the starch comprises wheat starch.

7. The method as set forth in claim 3 wherein the solvent exchange of the water in the starch hydrogel with an ethanolic curcumin solution to form an alcogel comprises immersing the starch hydrogel in the ethanolic curcumin solution.

8. The method as set forth in claim 7 wherein the ethanolic curcumin solution comprises from about 30% v/v to 100% v/v ethanol.

9. The method as set forth in claim 7 wherein the curcumin concentration of the ethanolic curcumin solution at room temperature is about 4.4±0.2 mg/mL.

10. The method as set forth in claim 7 wherein the curcumin concentration of the ethanolic curcumin solution at 60° C. is about 17.2±0.3 mg/mL.

11. The method as set forth in claim 3 wherein the $SC-CO_2$ drying of the alcogel to form the aerogel comprises $SC-CO_2$ extraction.

12. A method of reducing inflammation by administering the nanoporous starch aerogel of claim 1 to a subject.

13. A method of treating an inflammatory disease or disorder by administering the nanoporous starch aerogel of claim 1 to a subject.

14. The method as set forth in claim 13, wherein the inflammatory disease or disorder is selected from the group consisting of cancer and inflammatory bowel disease.

* * * * *